United States Patent [19]
Adair et al.

[11] Patent Number: 5,929,901
[45] Date of Patent: Jul. 27, 1999

[54] REDUCED AREA IMAGING DEVICES INCORPORATED WITHIN SURGICAL INSTRUMENTS

[76] Inventors: Edwin L. Adair, 317 Paragon Way, Castle Pines Village, Colo. 80104; Jeffrey L. Adair, 1861 E. Redfox Pl., Highlands Ranch, Colo. 80126; Randall S. Adair, 3082 S. Flamingo Way, Denver, Colo. 80222

[21] Appl. No.: 08/944,322

[22] Filed: Oct. 6, 1997

[51] Int. Cl.[6] .............................. H04N 7/18; A62B 1/04
[52] U.S. Cl. ................................ 348/76; 348/65; 348/70; 348/72; 600/109; 600/110; 600/112
[58] Field of Search ................................. 348/65, 66, 68, 348/70, 72, 76; 600/109, 110, 112, 173, 118; 358/98

[56] References Cited

U.S. PATENT DOCUMENTS

| Re. 33,854 | 3/1992 | Adair | 128/6 |
|---|---|---|---|
| 4,745,471 | 5/1988 | Takamura et al. | 358/98 |
| 4,786,965 | 11/1988 | Yabe | 358/98 |
| 4,814,648 | 3/1989 | Hynecek | 307/497 |
| 4,854,302 | 8/1989 | Allred, III | 128/6 |
| 4,869,246 | 9/1989 | Adair | 128/303.1 |
| 5,116,317 | 5/1992 | Carson, Jr. et al. | 604/96 |
| 5,162,913 | 11/1992 | Chatenever et al. | 358/209 |
| 5,220,198 | 6/1993 | Tsuji | 257/731 |
| 5,251,613 | 10/1993 | Adair | 128/6 |
| 5,381,784 | 1/1995 | Adair | 128/6 |
| 5,402,768 | 4/1995 | Adair | 128/4 |
| 5,471,515 | 11/1995 | Fossum et al. | 377/60 |
| 5,489,256 | 2/1996 | Adair | 600/133 |
| 5,605,531 | 2/1997 | Lane et al. | 600/118 |
| 5,630,782 | 5/1997 | Adair | 600/133 |
| 5,630,783 | 5/1997 | Steinberg | 600/158 |
| 5,682,199 | 10/1997 | Lankford | 348/72 |
| 5,701,155 | 12/1997 | Wood et al. | 348/72 |
| 5,734,418 | 3/1998 | Danna | 348/76 |
| 5,754,313 | 5/1998 | Pelchy et al. | 348/76 |

FOREIGN PATENT DOCUMENTS 0 492 349 A1   7/1992   European Pat. Off. .

OTHER PUBLICATIONS

"NASA's Tiny Camera Has a Wide–Angle Future"—Business Week, Mar. 6, 1995.

*Primary Examiner*—Anand S. Rao
*Attorney, Agent, or Firm*—Fields and Johnson, P.C.

[57] ABSTRACT

A reduced area imaging device is provided for use in medical or dental instruments such as an endoscope. In one configuration of the imaging device, the image sensor is placed remote from the remaining circuitry. In another configuration, all of the circuitry to include the image sensor is placed in a stacked fashion at the same location. In a first embodiment of the invention, the entire imaging device can be placed at the distal tip of an endoscope. In a second embodiment, the image sensor is remote from the remaining circuitry according to the first configuration, and wherein a control box can be provided which communicates with the image sensor and is placed remotely from the endoscope. In yet another embodiment, the imaging device can be incorporated in the housing of a standard medical camera which is adapted for use with traditional rod lens endoscopes. In any of the embodiments, the image sensor may be placed alone on a first circuit board, or timing and control circuits may be included on the first circuit board containing the image sensor. One or more video processing boards can be stacked in a longitudinal fashion with respect to the first board, or the video processing boards may be placed in the control box.

15 Claims, 11 Drawing Sheets

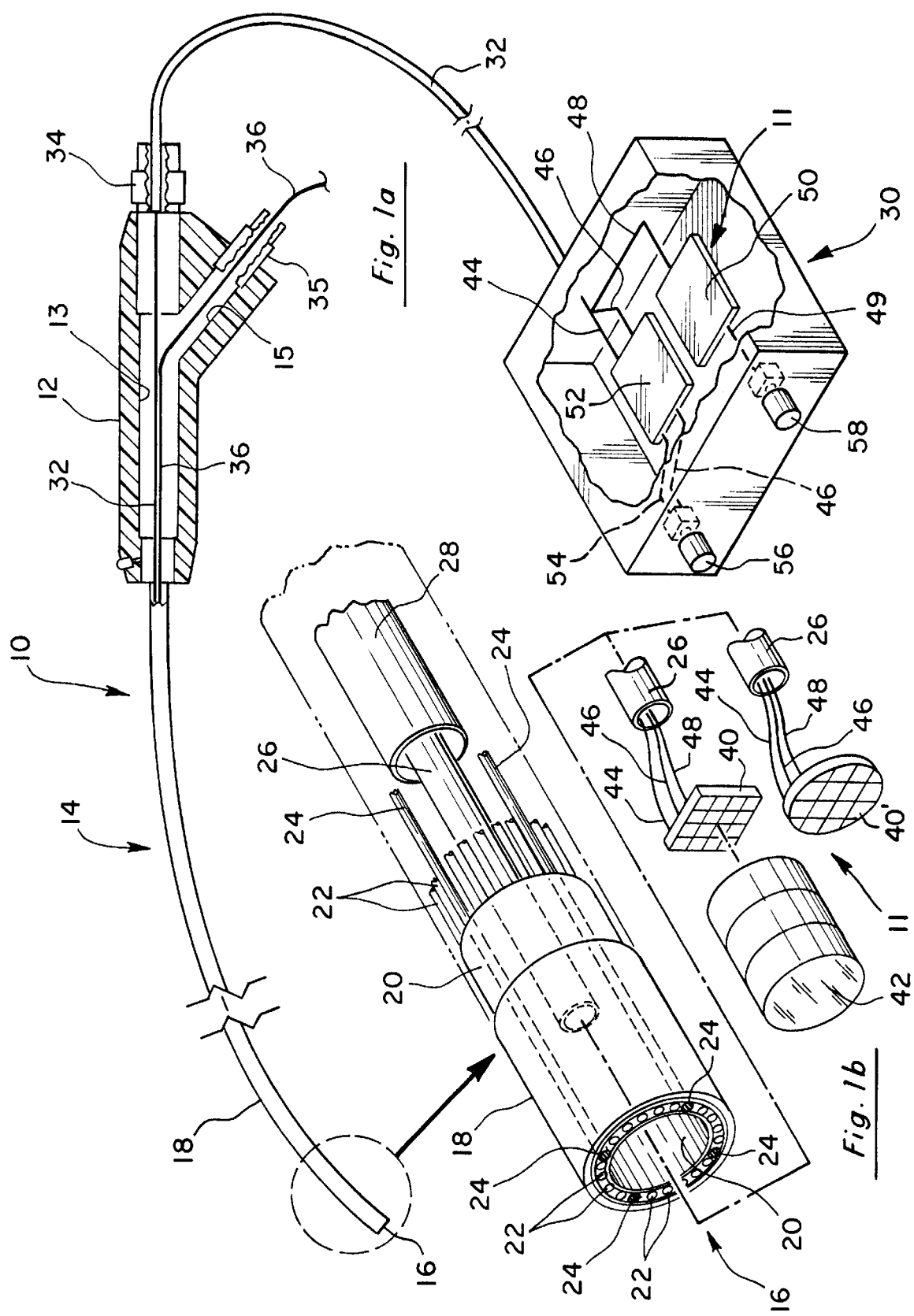

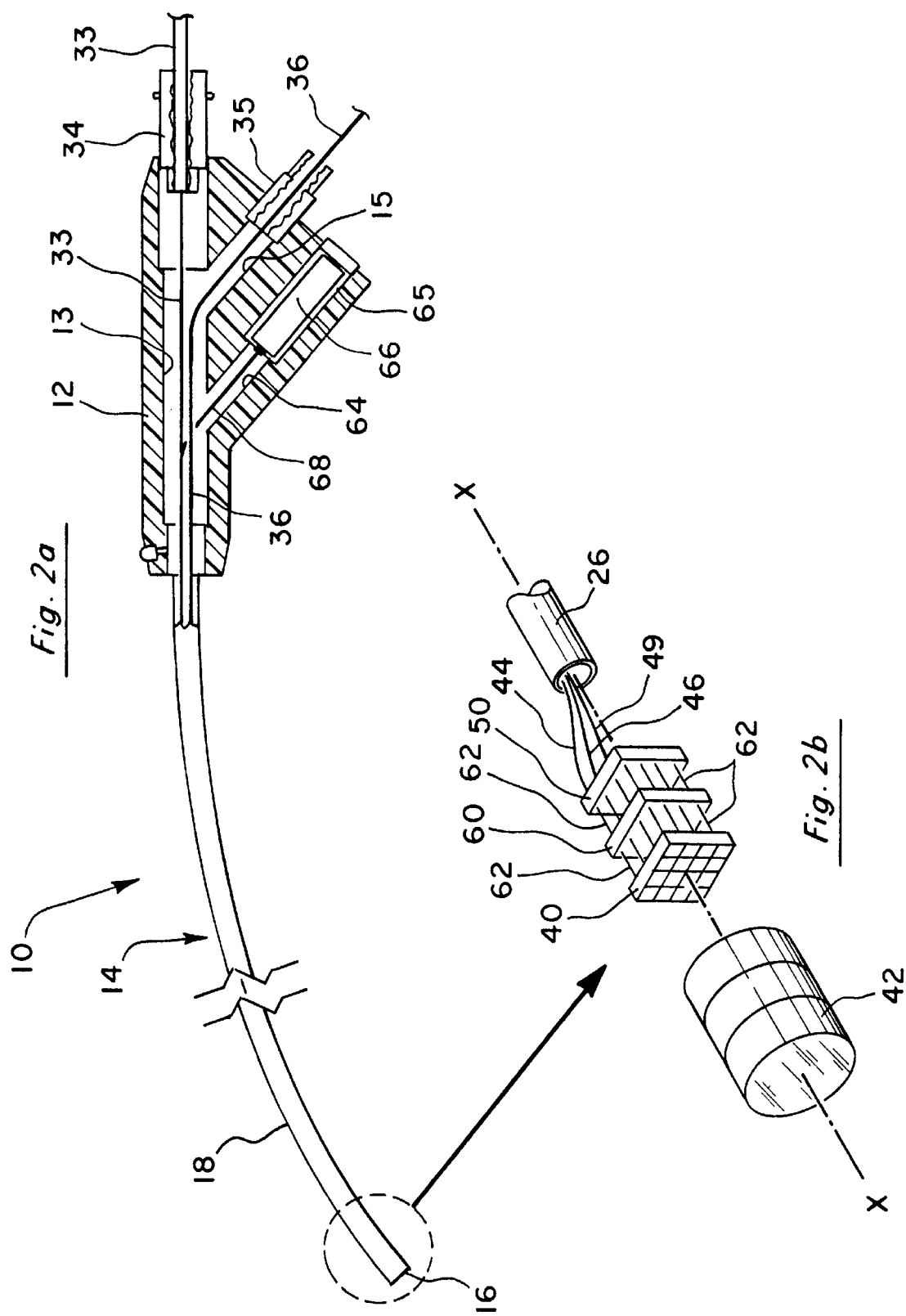

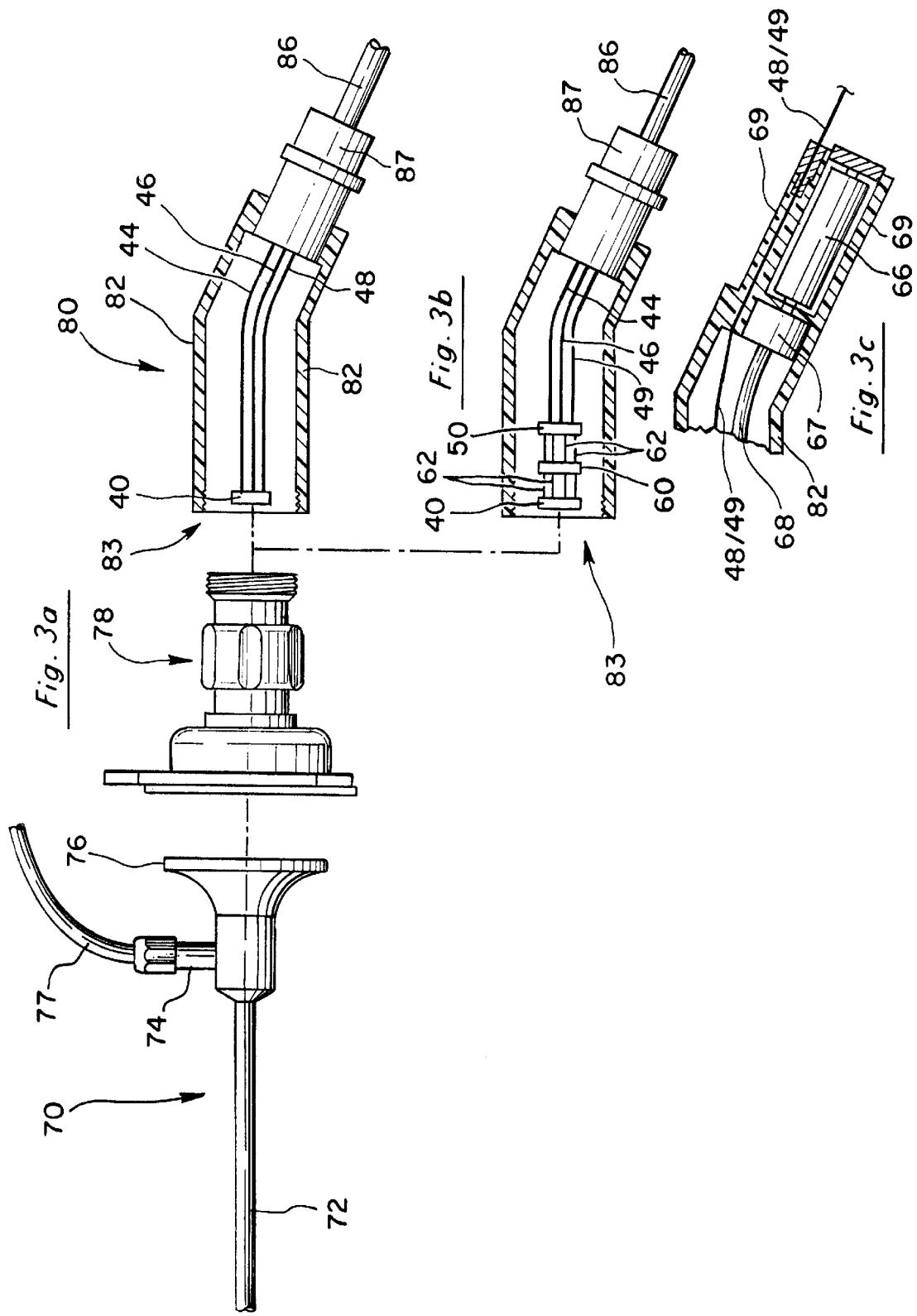

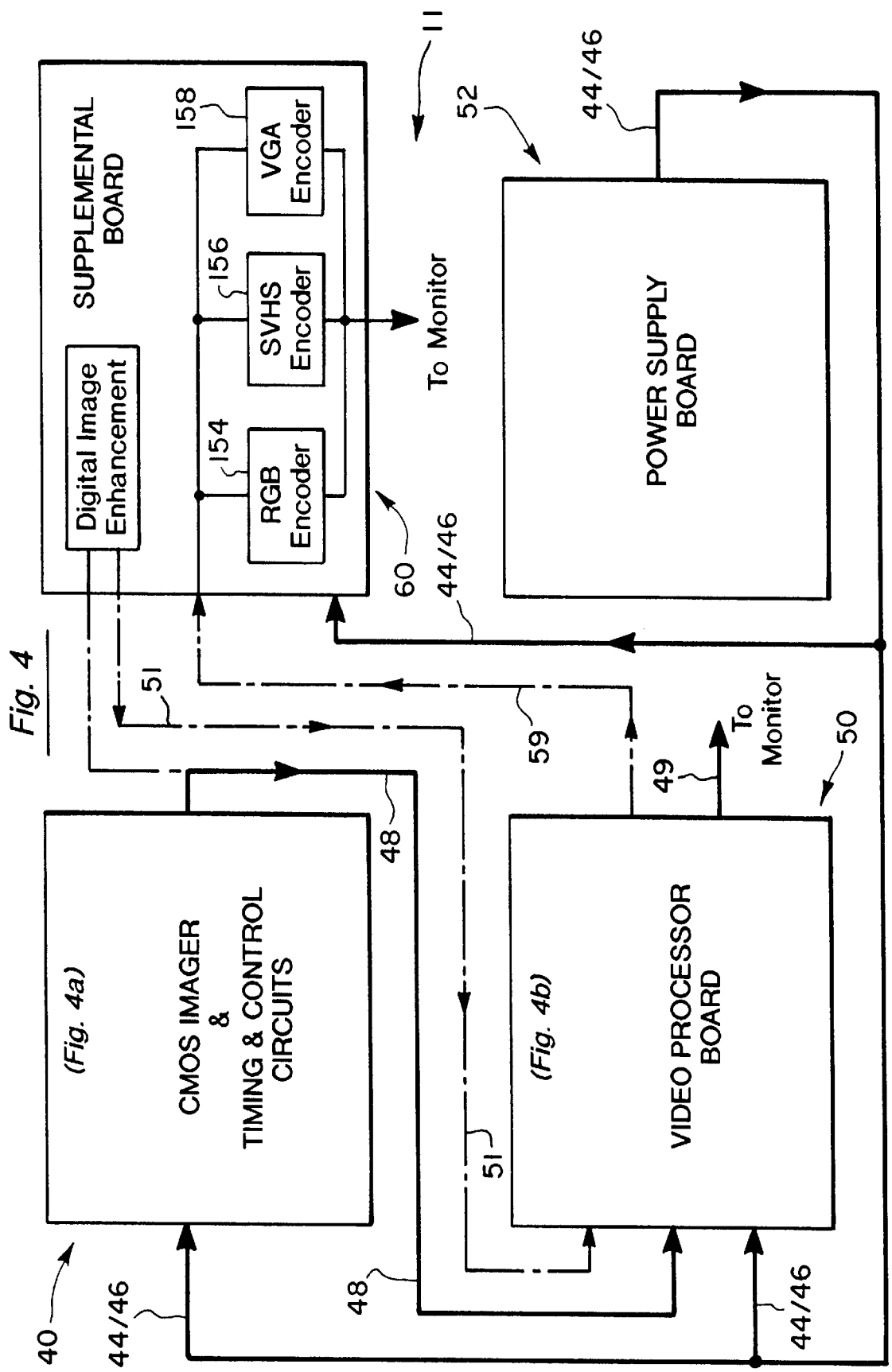

REDUCED AREA IMAGING DEVICES INCORPORATED WITHIN SURGICAL INSTRUMENTS

TECHNICAL FIELD

This invention relates to surgical instruments that incorporate the use of very small image sensors and associated electronics, and more particularly, to surgical instruments such as endoscopes having an inherent imaging capability in the form of complementary metal oxide, semiconductor integrated circuit sensors including active pixel arrays and accompanying processing circuitry.

BACKGROUND ART

In recent years, endoscopic surgery has become the accepted standard for conducting many types of surgical procedures, both in the medical and dental arenas. The availability of imaging devices enabling a surgeon or dentist to view a particular surgical area through a small diameter endoscope which is introduced into small cavities or openings in the body results in much less patient trauma as well as many other advantages.

In many hospitals, the rod lens endoscope is still used in endoscopic surgery. The rod lens endoscope includes a very precise group of lenses in an elongate and rigid tube which are able to accurately transmit an image to a remote camera in line with the lens group. The rod lens endoscope, because of its cost of manufacture, failure rate, and requirement to be housed within a rigid and straight housing, is being increasingly replaced by solid state imaging technology which enables the image sensor to be placed at the distal tip of the investigating device. The three most common solid state image sensors include charged coupled devices (CDD), charge injection devices (CID) and photo diode arrays (PDA). In the mid-1980s, complementary metal oxide semiconductors (CMOS) were developed for industrial use. CMOS imaging devices offer improved functionality and simplified system interfacing. Furthermore, many CMOS imagers can be manufactured at a fraction of the cost of other solid state imaging technologies.

One particular advance in CMOS technology has been in the active pixel-type CMOS imagers which consist of randomly accessible pixels with an amplifier at each pixel site. One advantage of active pixel-type imagers is that the amplifier placement results in lower noise levels than CCDs or other solid state imagers. Another major advantage is that these CMOS imagers can be mass produced on standard semiconductor production lines. One particularly notable advance in the area of CMOS imagers including active pixel-type arrays is the CMOS imager described in U.S. Pat. No. 5,471,515 to Fossum, et al. This CMOS imager can incorporate a number of other different electronic controls that are usually found on multiple circuit boards of much larger size. For example, timing circuits, and special functions such as zoom and anti-jitter controls can be placed on the same circuit board containing the CMOS pixel array without significantly increasing the overall size of the host circuit board. Furthermore, this particular CMOS imager requires 100 times less power than a CCD-type imager. In short, the CMOS imager disclosed in Fossum, et al. has enabled the development of a "camera on a chip."

Although the camera on a chip concept is one which has great merit for application in many industrial areas, a need still exists for a reduced area imaging device which can be used in even the smallest type of endoscopic instruments in order to view areas in the body that are particularly difficult to access, and to further minimize patient trauma by an even smaller diameter invasive instrument.

It is one object of this invention to provide surgical instruments with reduced area imaging devices which take advantage of the CMOS-type imagers of Fossum, et al., but rearrange the accompanying circuitry in a stacked relationship so that there is a minimum profile presented when used within the surgical instrument. It is another object of this invention to provide low cost imaging devices which may be "disposable." It is yet another object of this invention to provide a reduced area imaging device which may be used in conjunction with standard endoscopes by placing the imaging device through channels which normally receive other surgical devices, or receive liquids or gases for flushing a surgical area. It is yet another object of this invention to provide a surgical device with inherent imaging capability which may be battery powered and only requires one conductor for transmitting a pre-video signal to video processing circuitry within or outside the sterile field of the surgical area.

In addition to the intended use of the foregoing invention with respect to surgical procedures conducted by medical doctors, it is also contemplated that the invention described herein has great utility with respect to oral surgery and general dental procedures wherein a very small imaging device can be used to provide an image of particularly difficult to access locations. Additionally, while the foregoing invention has application with respect to the medical and dental fields, it will also be appreciated by those skilled in the art that the small size of the imaging device set forth herein can be applied to other functional disciplines wherein the imaging device can be used to view difficult to access locations for industrial equipment and the like. Therefore, the imaging device of this invention could be used to replace many industrial boroscopes.

The CMOS image sensor technology can be furthered improved with respect to reducing the profile area of the "camera on a chip" and incorporating such a reduced area imaging device into very small investigative instruments which can be used in the medical, dental, or industrial fields.

DISCLOSURE OF THE INVENTION

In accordance with the present invention, surgical instruments incorporating reduced area imaging devices are provided. The term "imaging device" as used herein describes the imaging elements and processing circuitry which is used to produce a video signal which may be accepted by a standard video device such as a television or video monitor accompanying a personal computer. The term "image sensor" as used herein describes the CMOS pixel array which captures images and stores them within the structure of each of the pixels in the array. This term also includes the timing and control circuits which enable the stored images to be retrieved from the pixel array. As further discussed below, the timing and control circuits can either be placed on the same planar substrate as the pixel array and the image sensor can therefore also be defined as an integrated circuit, or the timing and control circuits can be placed remote from the pixel array. The terms "signal" or "image signal" as used herein, and unless otherwise more specifically defined, refer to an image which at some point during its processing by the imaging device, is found in the form of electrons which have been placed in a specific format or domain. The term "processing circuitry" as used herein refers to the electronic components within the imaging device which receive the image signal from the image sensor and ultimately place the image signal in a usable format. The terms "timing and control circuits or circuitry" as used herein refer to the electronic components which control the release of the image signal from the pixel array.

In a first embodiment, the image sensor, with or without the timing and control circuitry, may be placed at the distal tip of the endoscopic instrument while the remaining processing circuitry may be found in a small remote control box which may communicate with the image sensor by a single cable.

In a second embodiment, the image sensor and the processing circuitry may all be placed in a stacked arrangement of circuit boards and positioned at the distal tip of the endoscopic instrument. In this embodiment, the pixel array of the image sensor may be placed by itself on its own circuit board while the timing and control circuitry and processing circuitry are placed on one or more other circuit boards. Alternatively, the circuitry for timing and control may be placed with the pixel array on one circuit board, while the remaining processing circuitry can be placed on one or more of the other circuit boards.

In yet another embodiment, the imaging device may be adapted for use with a standard rod lens endoscope wherein the imaging device is placed within a standard camera housing which is configured to connect to a standard "C" or "V" mount connector.

A generic endoscope may be used in the first and second embodiments which includes a very small diameter tubular portion which is inserted within the patient. The tubular portion may be made of a flexible material having a central lumen or opening therein for receiving the elements of the imaging device. The tubular portion may be modified to include an additional concentric tube placed within the central lumen and which enables a plurality of light fibers to be placed circumferentially around the periphery of the distal end of the tubular portion. Additionally, control wires may extend along the tubular portion in order to make the endoscope steerable. The material used to make the endoscope can be compatible with any desired sterilization protocol, or the entire endoscope can be made sterile and disposable after use.

For the configuration of the imaging device which calls for the array of pixels and the timing and control circuitry to be placed on the same circuit board, only one conductor is required in order to transmit the image signal to the processing circuitry. In the other configuration of the imaging device wherein the timing and control circuits are incorporated onto other circuit boards, a plurality of connections are required in order to connect the timing and control circuitry to the pixel array and the one conductor is also required to transmit the image signal.

BRIEF DESCRIPTION OF THE DRAWINGS

FIG. 1a illustrates a first embodiment including a fragmentary cross-sectional view of a generic endoscopic instrument, and a fragmentary perspective view of a control box, the endoscope and control box each incorporating elements of a reduced area imaging device;

FIG. 1b is an enlarged fragmentary partially exploded perspective view of the distal end of the endoscopic instrument specifically illustrating the arrangement of the image sensor with respect to the other elements of the tubular portion of the endoscope;

FIG. 2a is a fragmentary cross-sectional view of a second embodiment of this invention illustrating another generic endoscope wherein the imaging device is incorporated in its entirety at the distal tip of the endoscope;

FIG. 2b is an enlarged fragmentary partially exploded perspective view of the distal end of the endoscope of FIG. 2a illustrating the imaging device;

FIG. 3a is an elevational fragmentary cross-sectional view of the image sensor incorporated with a standard camera housing for connection to a rod lens endoscope;

FIG. 3b is a fragmentary cross-sectional view of the imaging device incorporated within the camera housing of FIG. 3a;

FIG. 3c is a fragmentary cross-sectional view similar to that of FIG. 3b illustrating a battery as an alternate source of power;

FIG. 4 is a schematic diagram of the functional electronic components which make up the imaging device;

BEST MODE FOR CARRYING OUT THE INVENTION

Figure 4A:
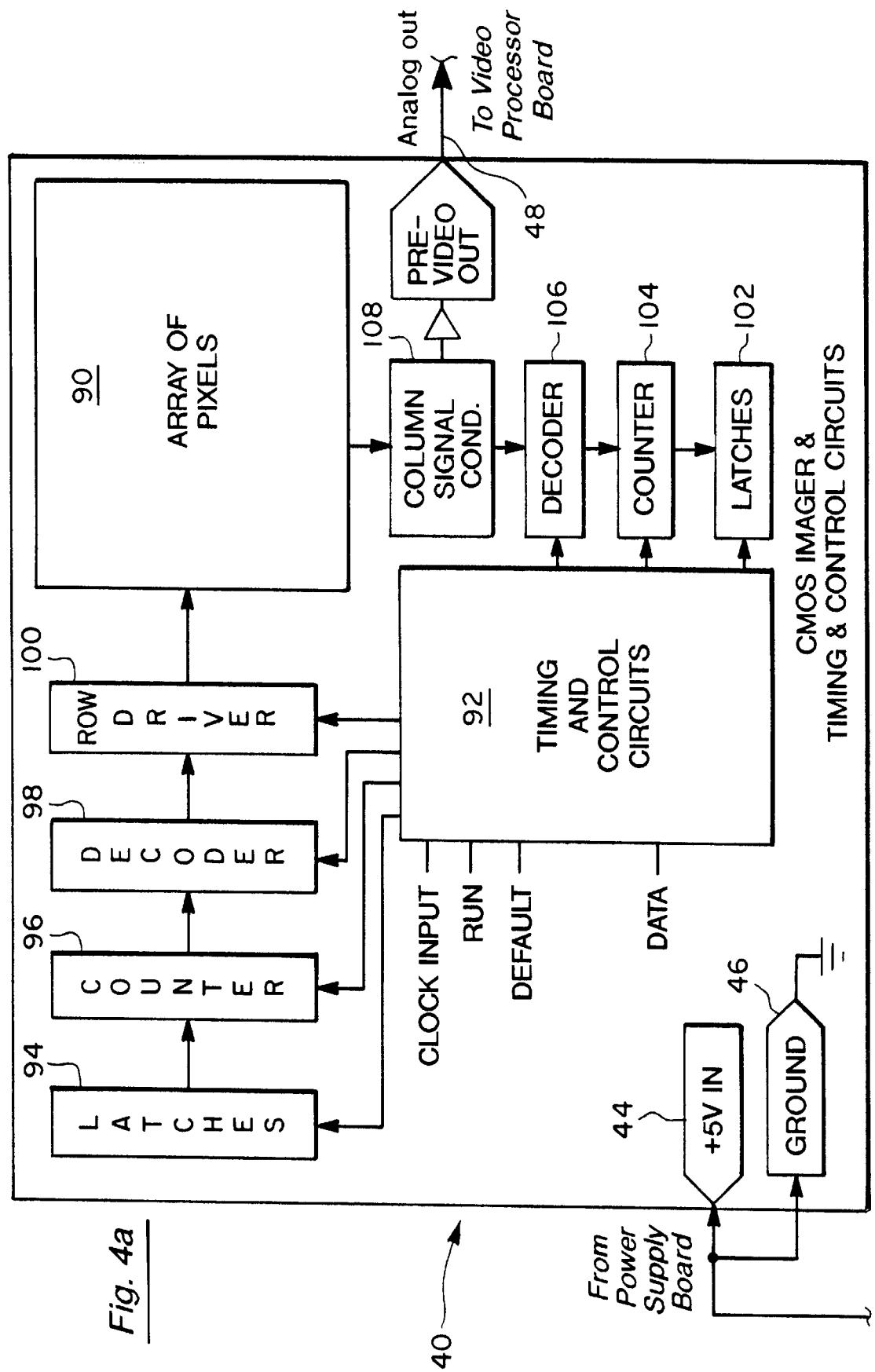
FIG. 4a is an enlarged schematic diagram of a circuit board which may include the array of pixels and the timing and control circuitry.

In accordance with one embodiment of the invention as shown in FIG. 1a, an endoscope 10 is provided which incorporates a reduced area imaging device 11, shown in FIG. 1b. As further discussed below, the elements of the imaging device may all be found at one location or the elements may be separated from one another and interconnected by the appropriate cable(s). The array of pixels making up the image sensor captures images and stores them in the form of electrical energy by conversion of light photons to electrons. This conversion takes place by the photo diodes in each pixel which communicate with one or more capacitors which store the electrons. The structure of the endoscope 10 includes a flexible or rigid tubular portion 14 which is inserted into the body of the patient and is placed at the appropriate location for viewing a desired surgical area. The tubular portion 14 attaches at its proximal end to a handle portion 12 which may be grasped by a surgeon who is conducting the endoscopic procedure. The handle 12 may include a central lumen or channel 13 which receives therethrough one or more cables or other structures which extend to the distal end 16 of tubular portion 14. Handle portion 12 may further include a supplementary channel 15 which intersects with central channel 13 and which may provide another point of entry for other cables, fluids or operative instruments to be placed through the endoscope.

FIG. 1b illustrates the distal end of the endoscope 16. The distal end 16 may be characterized by an outer tube 18 which traverses the length of the tubular portion 14 and connects to the handle portion 12. Placed concentrically within the outer tube 18 may be one or more inner tubes 20. In FIG. 1b, the gap between inner tube 20 and outer tube 18 forms a space in which one or more light fibers 22 or control wires 24 may be placed. As well understood by those skilled in the art, a plurality of circumferentially spaced light fibers as illustrated in FIG. 1b can be used to illuminate the surgical site. Additionally, the control wires 24 may communicate with a control mechanism (not shown) integrated on the handle portion 12 for manipulating the distal end 16 of the endoscope in a desired direction. The flexible tubular portion 14 coupled with a steerable feature enables the endoscope to be placed within winding bodily passages or other locations difficult to reach within the body.

An image sensor 40 may be placed within the central channel defined by inner tube 20. In the configuration shown in FIG. 1b, a cable 26 is used to house the conductors which communicate with the image sensor 40. An intermediate support tube 28 may be placed concentrically outside of cable 26 and concentrically within inner tube 20 to provide the necessary support for the cable 26 as it traverses through the inner channel defined by inner tube 20. In lieu of support tube 28, other well-known means may be provided to stabilize the cable 26 such as clips or other fastening means which may attach to the inner concentric surface of inner tube 20.

A control box 30 may be placed remote from the endoscope 10. The control box 30 contains some of the processing circuitry which is used to process the image signal produced by image sensor 40. Therefore, the imaging device 11 as previously defined would include the processing circuitry within control box 30 and the image sensor 40 located at the distal tip of the endoscope. Control box 30 communicates with image sensor 40 by means of cable 32 which may simply be an insulated and shielded cable which houses therein cable 26. Cable 32 is stabilized with respect to the handle portion 12 by means of a fitting 34 which ensures that cable 32 cannot be inadvertently pushed or pulled within channel 13. Additionally, an additional fitting 35 may be provided to stabilize the entry of a light cable 36 which houses the plurality of light fibers 22.

Image sensor 40 is illustrated as being a planar and square shaped member. However, the image sensor may be modified to be in a planar and circular shape to better fit within the channel defined by inner tube 20. Accordingly, FIG. 1b further shows an alternate shaped image sensor 40' which is round. A lens group or system 42 may be incorporated at the distal end of the endoscope in order to manipulate the image prior to it being impinged upon the array of pixels on the image sensor 40. This lens system 42 may be sealed at the distal end 16 of the endoscope so that the tubular portion 14 is impervious to fluids entering through the distal end 16. In the configuration of the imaging device 11 in FIGS. 1a and 1b, there are only three conductors which are necessary for providing power to the image sensor 40, and for transmitting an image from the image sensor 40 back to the processing circuitry found within control box 30. Namely, there is a power conductor 44, a grounding conductor 46, and an image signal conductor 48 each of which are hard wired to the image sensor. Thus, cable 26 may simply be a three-conductor 50 ohm cable.

Image sensor 40 can be as small as 1 mm in its largest dimension. However, a more preferable size for most endoscopic procedures would dictate that the image sensor 40 be between 4 mm to 8 mm in its largest dimension. The image signal transmitted from the image sensor through conductor 48 is also herein referred to as a pre-video signal. Once the pre-video signal has been transmitted from image sensor 40 by means of conductor 48, it is received by video processing board 50. Video processing board 50 then carries out all the necessary conditioning of the pre-video signal and places it in a form so that it may be viewed directly on a standard video device, television or standard computer video monitor. The signal produced by the video processing board 50 can be further defined as a post-video signal which can be accepted by a standard video device. As shown in FIG. 1a, a conductor 49 is provided which transmits the post-video signal to an output connector 58 on the exterior surface of control box 30. The cable (not shown) extending from the desired video device (not shown) may receive the post-video signal by means of connector 58. Power supply board 52 may convert incoming power received through power source 54 into the desired voltage. In the preferred CMOS imager incorporated in this invention, the power to the imaging device is simply a direct current which can be a 1.5 volt to a 12 volt source. Incoming power from, for example, a wall receptacle, communicates with power supply board 52 by connector 56. Power supply board 52 takes the incoming power source and regulates it to the desired level. Additionally, ground 46 is also shown as extending back to the source of power through connector 56.

FIG. 2a illustrates a second embodiment of this invention wherein the imaging device is self-contained entirely within the distal end 16 of the endoscope, and a power source which drives the circuitry within the imaging device may come from a battery 66 housed within handle portion 12.

As shown in FIG. 2b, the video processing board 50 may be placed directly behind image sensor 40. A plurality of pin connectors 62 serve to electrically couple image sensor 40 with video processing board 50 depending upon the specific configuration of image sensor 40, pin connectors 62 may be provided either for structural support only, or to provide a means by which image signals are transmitted between image sensor 40 and board 50. When necessary, one or more supplementary boards 60 may be provided which further contain processing circuitry to process the image signal and present it in a form which may be directly received by a desired video device. The area which is occupied by image sensor 40 may be defined as the profile area of the imaging device and which determines its critical dimensions. Any imaging elements that are found on boards 50 or 60 must be able to be placed on one or more circuit boards which are longitudinally aligned with image sensor 40 along longitudinal axis XX. If the profile area is not critical in terms of limiting the largest sized imaging element within the imaging device, then the additional circuit boards 50 and 60 which are normally placed in line with image sensor 40 can be aligned in an offset manner or may be larger than the profile area of image sensor 40. In the configuration of FIG. 2b, it is desirable that elements 40, 50 and 60 be approximately the same size so that they may fit uniformly within the central channel of the endoscope. Additionally, image sensor 40 may be bonded to lens system 42 in order to provide further structural support to the imaging device 11 when mounted within the distal end 16.

Referring back to the handle portion 12 in FIG. 2a, an additional channel 64 may be provided in order that a power supply cable 68 may communicate with battery 66. Conveniently, battery 66 may itself be mounted within a well 65 formed in handle portion 12. Cable 68 carries the conductor 44 and ground 46. Cable 68 may intersect with cable 33 within channel 13, cables 68 and 33 extending then to the distal end 16. Cable 33 can be a single conductor cable which transmits the post-video signal to a desired video device. In other words, cable 33 may simply be an insulated and shielded housing for conductor 49 which carries the post-video signal. Because the preferred CMOS image sensor of the imaging device 11 only requires a 5 volt power supply, a battery is an ideal power source in lieu of a conductor which would trail the endoscope. Accordingly, the endoscope is made more mobile and easier to handle by eliminating at least one of the trailing cables.

FIG. 3a illustrates yet another preferred embodiment of this invention, wherein the imaging device can be used in conjunction with a standard rod lens endoscope 70. As shown, rod lens endoscope 70 includes a lens train 72 which includes a plurality of highly precise lenses (not shown) which are able to transmit an image from the distal end of the endoscope, to a camera in line with the endoscope. The rod lens endoscope is equipped with a light guide coupling post 74. Light guide post 74 connects to a source of light in the form of a cable 77 having a plurality of fiber optic strands (not shown) which communicate with a source of light (not shown). The most common arrangement of the rod lens endoscope also includes a "C" or "V" mount connector 78 which attaches to the eyepiece 76. The "C" or "V" mount attaches at its other end to a camera group 80. The camera group 80 houses one or more of the elements of the imaging device. In this embodiment, the small size of the imaging device is not a critical concern since the imaging device is not being placed at the distal end of the endoscope. However, the incorporation of the imaging device in a housing which would normally hold a traditional camera still provides an advantageous arrangement. As shown, the camera group 80 may include a housing 82 which connects to a power/video cable 86. Fitting 87 is provided to couple cable 86 to the interior elements of the camera group 80 found within housing 82. FIG. 3a illustrates an arrangement of the imaging device 11 wherein the image sensor 40 is placed by itself within the housing 82 and the processing circuitry of the imaging device can be positioned in a remote control box as shown in FIG. 1a. Accordingly, only three conductors 44, 46 and 48 are necessary for providing power to the image sensor 40 and for transmitting the pre-video signal to the control box. Alternatively, as shown in FIG. 3b, the entire imaging device 11 may be incorporated within camera group 80, each of the elements of the imaging device being placed in the stacked arrangement similar to FIG. 2b. As discussed above, size is not as much of a concern in the embodiment of FIG. 3a and 3b since the camera group housing 82 is much larger than the distal tip of the endoscope of FIGS. 1a and 2a.

FIG. 3c also illustrates the use of a battery 66 which provides source of power to the imaging device in either FIG. 3a or 3b. In this arrangement, housing 82 is altered to include a battery housing 69 which houses the battery 66 therein. Battery housing 69 may include a very small diameter channel which may allow conductor 48 or 49 to communicate directly with the processing circuitry or video device, respectively. It will also be understood that the embodiment in FIG. 1a may incorporate the use of a battery 66 as the source of power. Thus, handle 12 in FIG. 1a may be altered in the same way as housing 82 to allow a battery to be attached to the handle portion 12.

FIG. 4 is a schematic diagram illustrating one way in which the imaging device 11 may be constructed. As illustrated, the CMOS image sensor 40 may include the timing and control circuits on the same planar structure. Power is supplied to image sensor 40 by power supply board 52. The connection between image sensor 40 and board 52 may simply be a cable having two conductors therein, one for ground and another for transmitting the desired voltage. These are illustrated as conductors 44 and 46. The output from image sensor 40 in the form of the pre-video signal is input to video processor board 50 by means of the conductor 48. In the configuration of FIG. 4, conductor 48 may simply be a 50 ohm conductor. Power and ground also are supplied to video processing board 50 by conductors 44 and 46 from power supply board 52. The output signal from the video processor board 50 is in the form of the post-video signal and which may be carried by conductor 49 which can also be a 50 ohm conductor.

In the first embodiment illustrated in FIG. 1a, cable 32 can be used to house conductors 44, 46 and 48. In the embodiment shown in FIG. 2a, cable 33 can be used to house conductor 49 by itself when a battery power source is used, or alternatively, cable 33 may house conductors 44, 46 and 49 if the embodiment of FIG. 2a utilizes a power source from board 52.

Optionally, a supplementary processing board 60 may be provided to further enhance the pre-video signal. As shown in FIG. 4, the supplementary board 60 may be placed such that the pre-video signal from image sensor 40 is first sent to the supplementary board and then output to the video processor board 50. In this case, the output from board 50 can be carried along conductor 51. This output can be defined as an enhanced pre-video signal. Furthermore, the post-video signal from video processor board 50 may return to the supplementary board 60 for further processing, as further discussed below. The conductor used to transmit the post-video signal back to the supplementary board is shown as conductor 59. The power supply board 52 may also provide power to the supplementary board in the same manner as to image sensor 40 and board 50. That is, a simple hard-wired connection is made onto the supplementary board for the ground and voltage carrying conductors. As discussed above, image sensor 40 may be placed remotely from boards 50 and 60. Alternatively, image sensor 40, and boards 50 and 60 each may be placed within the distal end of the endoscope.

Although FIG. 4 illustrates the CMOS image sensor and the timing and control circuits being placed on the same planar structure, it is possible to separate the timing and control circuits from the pixel array and place the timing and control circuits onto video processing board 50. The advantage in placing the timing and control circuits on the same planar structure as the image sensor is that only three connections are required between image sensor 40 and the rest of the imaging device, namely, conductors 44, 46 and 48. Additionally, placing the timing and control circuits on the same planar structure with the pixel array results in the pre-video signal having less noise. Furthermore, the addition of the timing and control circuits to the same planar structure carrying the image sensor only adds approximately 0.25 millimeters to one dimension of the planar structure. If the pixel array is to be the only element on planar structure, then additional connections must be made between it and the video processing board 50 in order to transmit the clock signals and other control signals to the pixel array. For example, a ribbon-type cable (not shown) or a plurality of 50 ohm coaxial cables (not shown) must be used in order to control the downloading of information from the pixel array. Each of these additional connections would be hard wired between the boards.

FIG. 4a is a more detailed schematic diagram of image sensor 40 which contains an array of pixels 90 and the timing and control circuits 92. The preferred CMOS pixel array 90 is similar to that as disclosed in U.S. Pat. No. 5,471,515 to Fossum, et al., said patent being incorporated in its entirety by reference. More specifically, FIG. 3 of Fossum, et al. illustrates the circuitry which makes up each pixel in the array of pixels 90. The array of pixels 90 as described in Fossum, et al. is an active pixel group with intra-pixel charged transfer. The image sensor made by the array of pixels is formed as a monolithic complementary metal oxide semiconductor integrated circuit which may be manufactured in an industry standard complementary metal oxide semiconductor process. The integrated circuit includes a focal plane array of pixel cells, each one of the cells including a photo gate overlying the substrate for accumulating the photo generated charges. In broader terms, as well understood by those skilled in the art, an image impinges upon the array of pixels, the image being in the form of photons which strike the photo diodes in the array of pixels. The photo diodes or photo detectors convert the photons into electrical energy or electrons which are stored in capacitors found in each pixel circuit. Each pixel circuit has its own amplifier which is controlled by the timing and control circuitry discussed below. The information or electrons stored in the capacitors is unloaded in the desired sequence and at a desired frequency, and then sent to the video processing board 50 for further processing.

The timing and control circuits 92 are used to control the release of the image information or image signal stored in the pixel array. In the preferred image sensor of Fossum, et al., the pixels are arranged in a plurality of rows and columns. The image information from each of the pixels is first consolidated in a row by row fashion, and is then downloaded from one or more columns which contain the consolidated information from the rows. As shown in FIG. 4a, the control of information consolidated from the rows is achieved by latches 94, counter 96, and decoder 98. The operation of the latches, counter and decoder is similar to the operation of similar control circuitry found in other imaging devices. That is, a latch is a means of controlling the flow of electrons from each individual addressed pixel in the array of pixels. When a latch 94 is enabled, it will allow the transfer of electrons to the decoder 98. The counter 96 is programmed to count a discrete amount of information based upon a clock input from the timing and control circuits 92. When the counter 96 has reached its set point or overflows, the image information is allowed to pass through the latches 94 and be sent to the decoder 98 which places the consolidated information in a serial format. Once the decoder 98 has decoded the information and placed it in the serial format, then the row driver 100 accounts for the serial information from each row and enables each row to be downloaded by the column or columns. In short, the latches 94 will initially allow the information stored in each pixel to be accessed. The counter 96 then controls the amount of information flow based upon a desired time sequence. Once the counter has reached its set point, the decoder 98 then knows to take the information and place it in the serial format. The whole process is repeated, based upon the timing sequence that is programmed. When the row driver 100 has accounted for each of the rows, the row driver reads out each of the rows at the desired video rate.

The information released from the column or columns is also controlled by a series of latches 102, a counter 104 and a decoder 106. As with the information from the rows, the column information is also placed in a serial format which may then be sent to the video processing board 50. This serial format of column information is the pre-video signal carried by conductor 48. The column signal conditioner 108 places the column serial information in a manageable format in the form of desired voltage levels. In other words, the column signal conditioner 108 only accepts desired voltages from the downloaded column(s).

The clock input to the timing and control circuits 92 may simply be a quartz crystal timer. This clock input is divided into many other frequencies for use by the various counters. The run input to the timing and control circuit 92 may simply be an on/off control. The default input can allow one to input the pre-video signal to a video processor board which may run at a frequency of other than 30 hertz. The data input controls functions such as zoom. Since the CMOS active pixel array can be accessed in a random manner, features such as zoom are easily manipulated by addressing only those pixels which locate a desired area of interest by the surgeon.

A further discussion of the timing and control circuitry found on board 40 and incorporated with the pixel array 90 is described in an article entitled "Active Pixel Image Sensor Integrated With Readout Circuits" appearing in NASA Tech Briefs, pp. 38 and 39 of the October, 1996 publication. The disclosure of this particular article is also incorporated by reference herein.

Figure 4B:
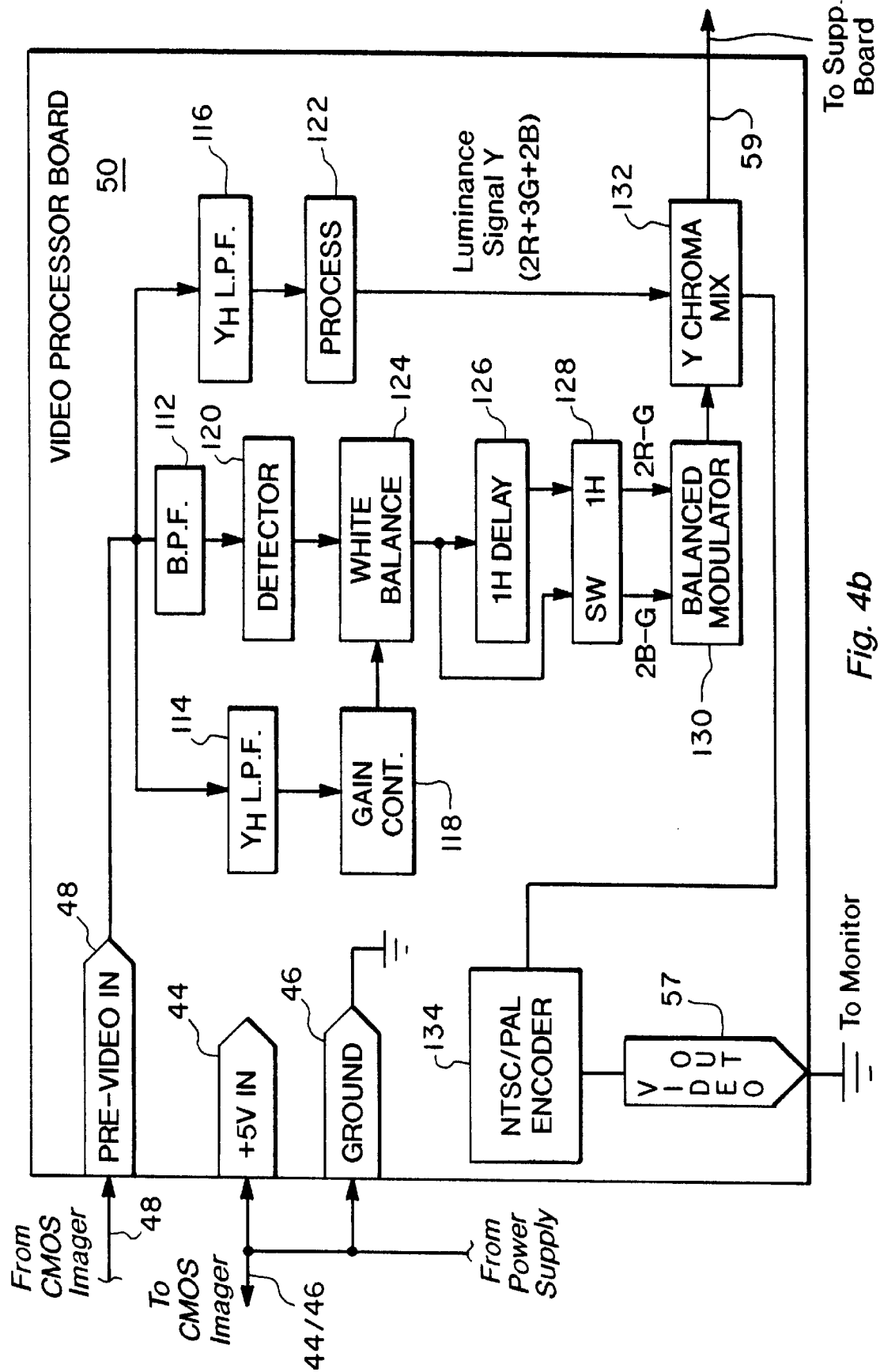
FIG. 4b is an enlarged schematic diagram of a video processing board having placed thereon the processing circuitry which processes the pre-video signal generated by the array of pixels and which converts the pre-video signal to a post-video signal which may be accepted by a standard video device.

Once image sensor 40 has created the pre-video signal, it is sent to the video processing board 50 for further processing. At board 50, as shown in FIG. 4b, the pre-video signal is passed through a series of filters. One common filter arrangement may include two low pass filters 114 and 116, and a band pass filter 112. The band pass filter only passes low frequency components of the signal. Once these low frequency components pass, they are then sent to detector 120 and white balance circuit 124, the white balance circuit distinguishing between the colors of red and blue. The white balance circuit helps the imaging device set its normal, which is white. The portion of the signal passing through low pass filter 114 then travels through gain control 118 which reduces the magnitude or amplitude of this portion to a manageable level. The output from gain control 118 is then fed back to the white balance circuit 124. The portion of the signal traveling through filter 116 is placed through the processor 122. In the processor 122, the portion of the signal carrying the luminance or non-chroma is separated and sent to the Y chroma mixer 132. Any chroma portion of the signal is held in processor 122.

Referring to the output of the white balance circuit 124, this chroma portion of the signal is sent to a delay line 126 where the signal is then further reduced by switch 128. The output of switch 128 is sent through a balanced modulator 130 and also to the Y chroma mixer 132 where the processed chroma portion of the signal is mixed with the processed nonchroma portion. Finally, the output from the Y chroma mixer 132 is sent to the NTSC/PAL encoder 134, commonly known in the art as a "composite" encoder. The composite frequencies are added to the signal leaving the Y chroma mixer 132 in encoder 134 to produce the post-video signal which may be accepted by a television.

Referring back to FIG. 4, it further illustrates supplementary board 60 which may be used to digitally enhance or otherwise further condition the pre-video signal produced from image sensor 40. For example, digital enhancement can brighten or otherwise clarify the edges of an image viewed on a video screen. Additionally, the background images may be removed thus leaving only the foreground images or vice versa. The connection between image sensor 40 and board 60 may simply be the conductor 48 which may also transfer the pre-video signal to board 50. Once the pre-video signal has been digitally enhanced on supplementary board 60, it is then sent to the video processor board 50 by means of another conductor 51. The pre-video signal is an analog signal. The digitally enhanced pre-video signal may either be a digital signal or it may be converted back to the analog domain prior to being sent to board 50.

In addition to digital enhancement, supplementary board 60 may further include other circuitry which may further condition the post-video signal so that it may be viewed in a desired format other than NTSC/PAL. As shown in FIGS. 4, intermediate conductor 59 may transmit the signal output from Y chroma mixer 132 back to the supplementary board 60 where the signal is further encoded for viewing in a particular format. One common encoder which can be used includes an RGB encoder 154. The RGB encoder separates the signal into three separate colors (red, green and blue) so that the surgeon may selectively choose to view only those images containing one or more of the colors. Particularly in tissue analysis where dyes are used to color the tissue, the RGB encoder may help the surgeon to identify targeted tissue.

The next encoder illustrated in FIG. 4 is a SVHS encoder 156 (super video home system). This encoder splits or separates the luminance portion of the signal and the chroma portion of the signal prior to entering the video device. Some observers believe that a cleaner signal is input to the video device by such a separation which in turn results in a more clear video image viewed on the video device. The last encoder illustrated in FIG. 4 is a VGA encoder 158 which enables the signal to be viewed on a standard VGA monitor which is common to many computer monitors.

One difference between the arrangement of image sensor 40 and the outputs found in FIG. 3 of the Fossum, et al. patent is that in lieu of providing two analog outputs [namely, VS out (signal) and VR out (reset)], the reset function takes place in the timing and control circuitry 92. Accordingly, the pre-video signal only requires one conductor 48.

FIGS. 5a–5e illustrate in more detail one example of circuitry which may be used in the video processing board 50 in order to produce a post-video signal which may be directly accepted by a video device such as a television. The circuitry disclosed in FIGS. 5a–5e is very similar to circuitry which is found in a miniature quarter-inch Panasonic camera, Model KS-162. It will be understood by those skilled in the art that the particular arrangement of elements found in FIGS. 5a–5e are only exemplary of the type of video processing circuitry which may be incorporated in order to take the pre-video signal and condition it to be received by a desired video device.

Figure 5A:
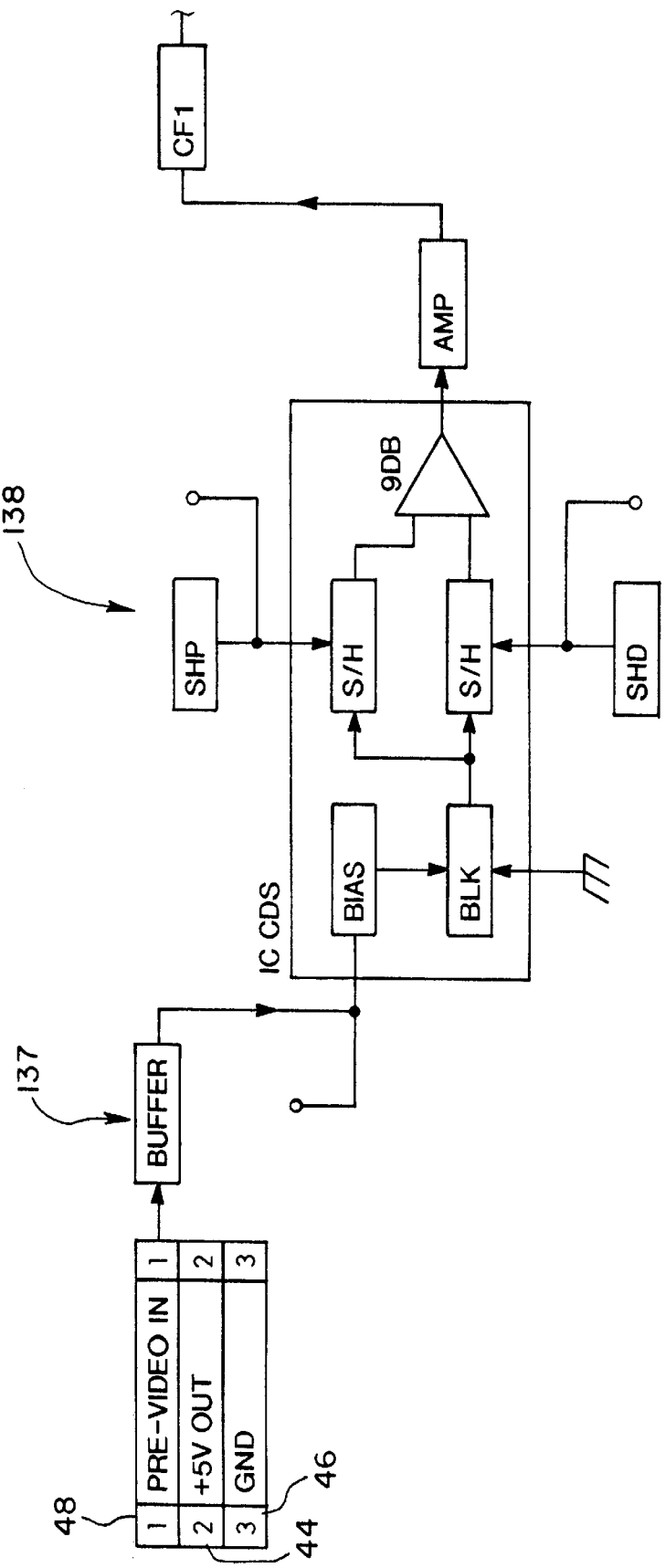
FIGS. 5a–5e are schematic diagrams that illustrate an example of specific circuitry which may be used to make the imaging device.

As shown in FIG. 5a, 5 volt power is provided along with a ground by conductors 44 and 46 to board 50. The pre-video signal carried by conductor 48 is buffered at buffer 137 and then is transferred to amplifying group 138. Amplifying group 138 amplifies the signal to a usable level as well as achieving impedance matching for the remaining circuitry.

Figure 5B:
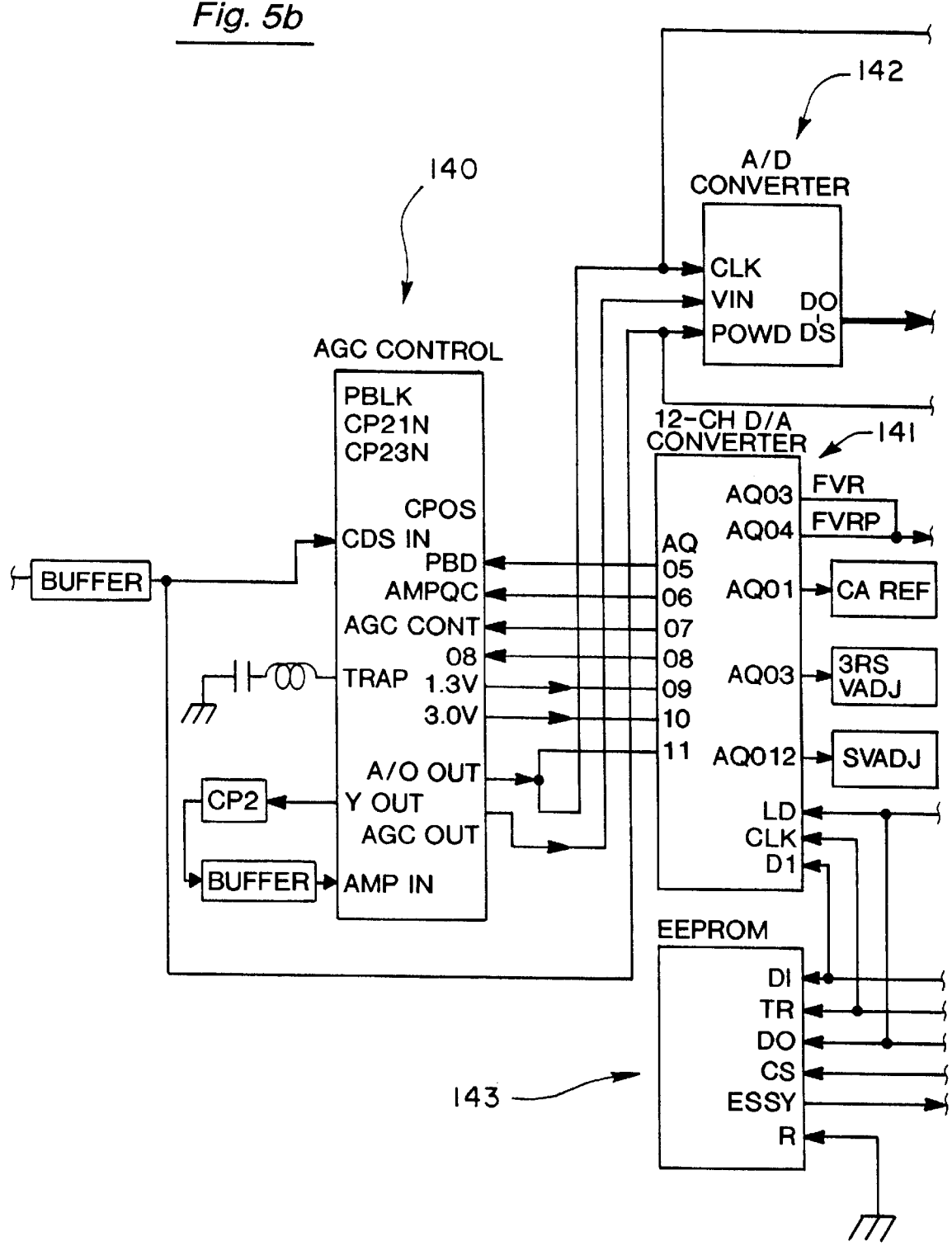

The next major element is the automatic gain control 140 shown in FIG. 5b. Automatic gain control 140 automatically controls the signal from amplifying group 138 to an acceptable level and also adds other characteristics to the signal as discussed below. More specifically, automatic gain control 140 conditions the signal based upon inputs from a 12 channel digital to analog converter 141. Converter 141 retrieves stored information from EEPROM (electrically erasable programmable read only memory) 143. EEPROM 143 is a non-volatile memory element which may store user information, for example, settings for color, tint, balance and the like. Thus, automatic gain control 140 changes the texture or visual characteristics based upon user inputs. The signal leaving the automatic gain control 140 is an analog signal until being converted by analog to digital converter 142.

Figure 5C:
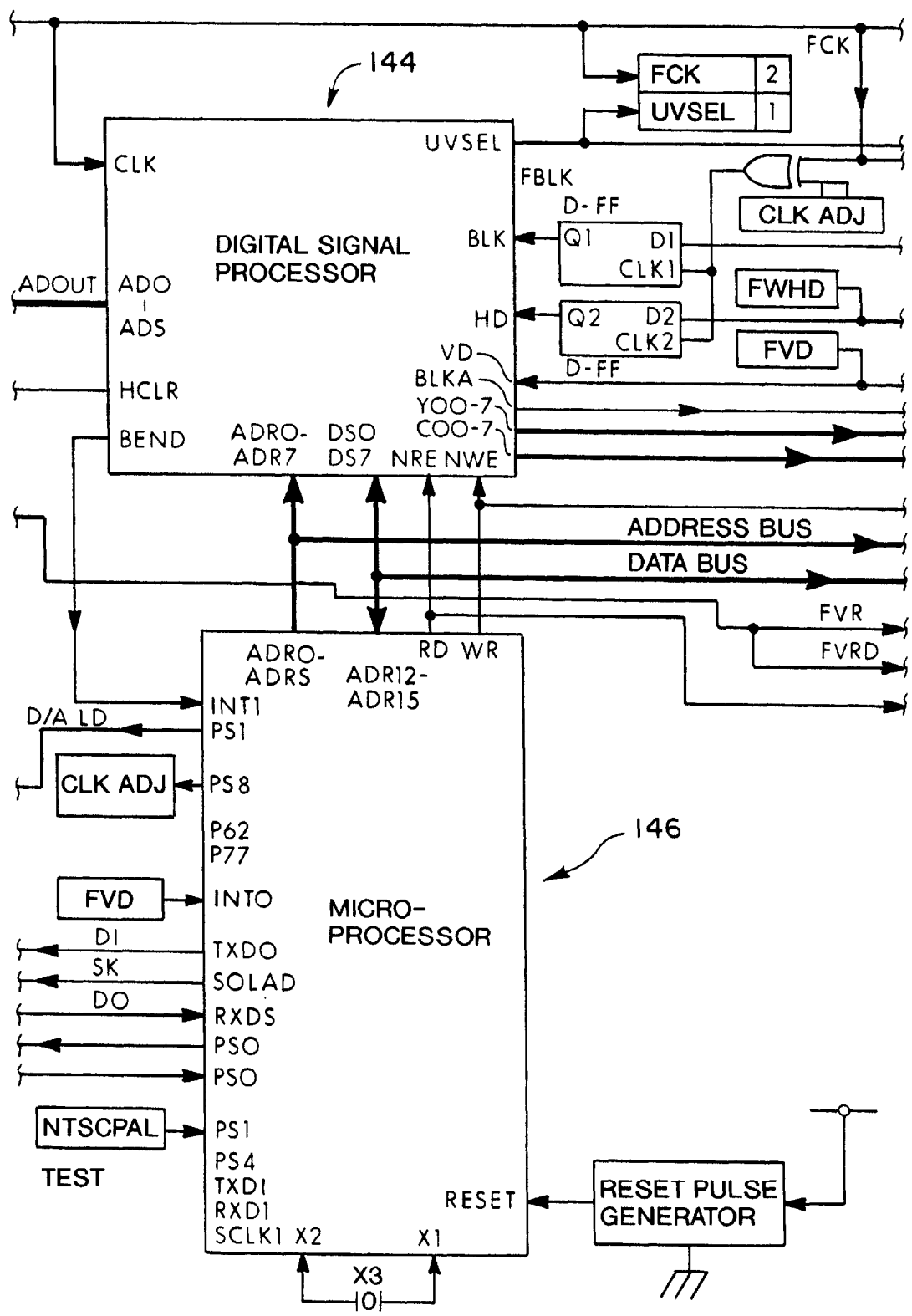

Digital signal processor 144 of FIG. 5c further processes the converted signal into a serial type digital signal. One function of the microprocessor 146 is to control the manner in which digital signal processor 144 sorts the digital signals emanating from converter 142. Microprocessor 146 also controls analog to digital converter 142 in terms of when it is activated, when it accepts data, when to release data, and the rate at which data should be released. Microprocessor 146 may also control other functions of the imaging device such as white balance. The microprocessor 146 may selectively receive the information stored in the EEPROM 143 and carry out its various commands to further control the other elements within the circuitry.

Figure 5D:
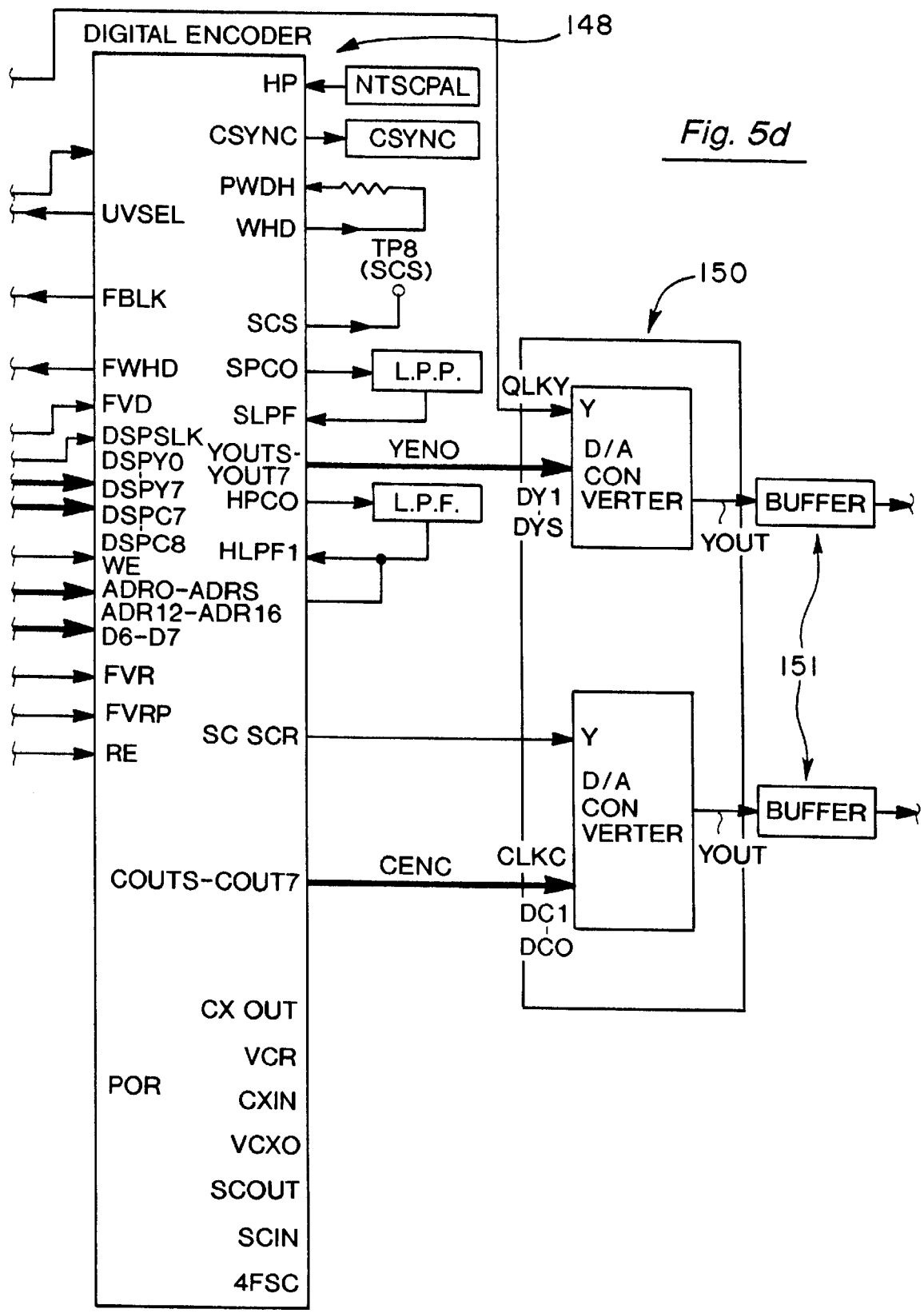

After the signal is processed by digital signal processor 144, the signal is sent to digital encoder 148 illustrated in FIG. 5d. Some of the more important functions of digital encoder 148 are to encode the digital signal with synchronization, modulated chroma, blanking, horizontal drive, and the other components necessary so that the signal may be placed in a condition for reception by a video device such as a television monitor. As also illustrated in FIG. 5d, once the signal has passed through digital encoder 148, the signal is reconverted into an analog signal through digital to analog converter 150.

Figure 5E:
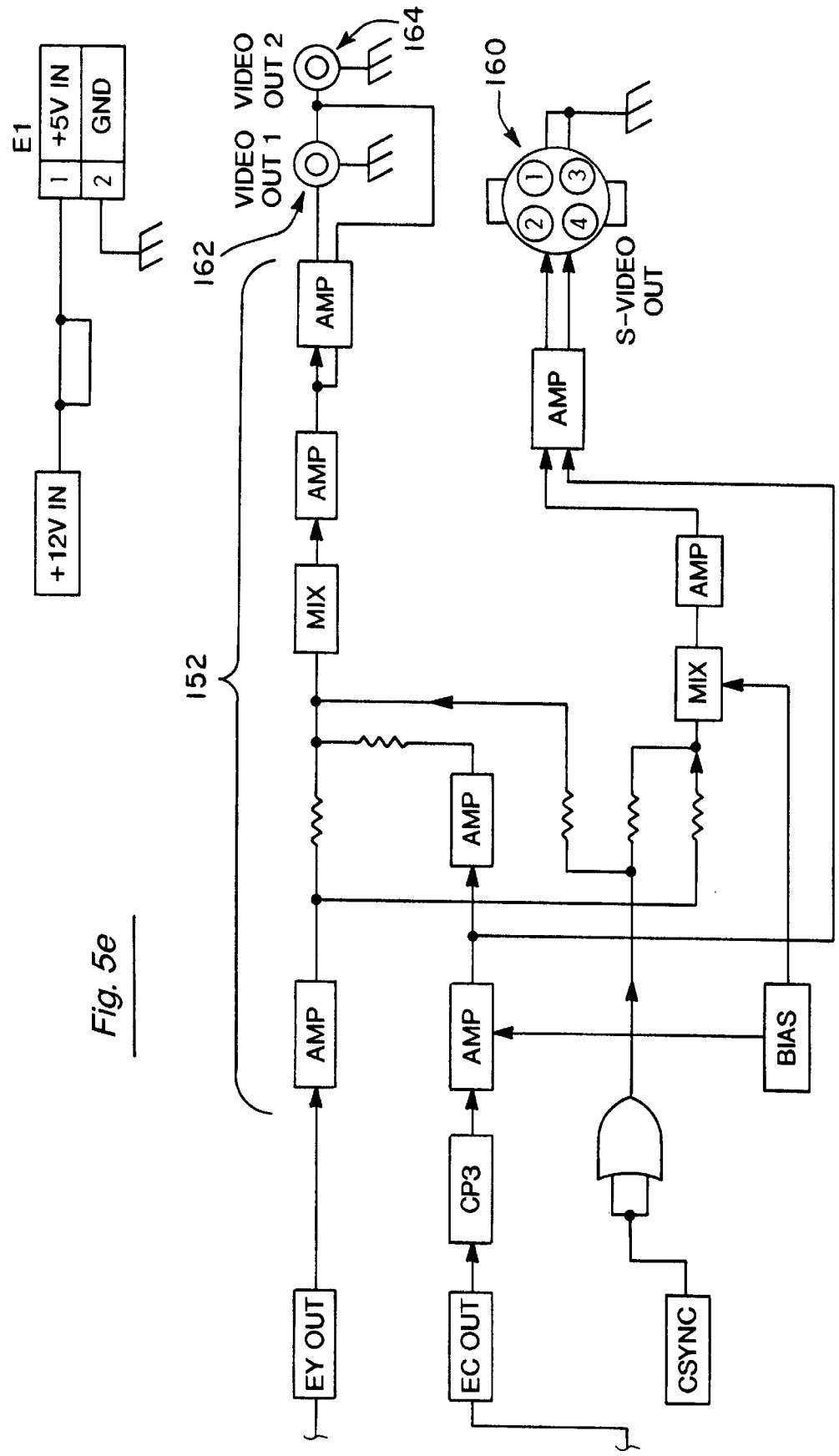

This reconverted analog signal is then buffered at buffers 151 and then sent to amplifier group 152 of FIG. 5e which amplifies the signal so that it is readily accepted by a desired video device. Specifically, as shown in FIG. 5e, one SVHS outlet is provided at 160, and two composite or NTSC outlets are provided at 162 and 164, respectively.

From the foregoing, it is apparent that an entire imaging device may be incorporated within the distal tip of an endoscope, or may have some elements of the imaging device being placed in a small remote box adjacent to the endoscope. Because of the particular type of CMOS image sensor used, the profile area of the imaging device is small enough to be placed into an endoscope which has a very small diameter tube. Additionally, the imaging device may be placed into the channels of existing endoscopes to provide additional imaging capability without increasing the size of the endoscope. The imaging device may be powered by a standard power input connection in the form of a power cord, or a small lithium battery may be used.

This invention has been described in detail with reference to particular embodiments thereof, but it will be understood that various other modifications can be effected within the spirit and scope of this invention.

What is claimed is:

1. A reduced area imaging device comprising:
   a first circuit board defining a profile area and lying in a first plane, said first circuit board including an array of CMOS pixels on said first plane for receiving images thereon and wherein individual CMOS pixels within said array of CMOS pixels each include an amplifier, said first circuit board further including circuitry means on said first plane and coupled to said array of CMOS pixels for timing and control of said array of CMOS pixels, said first circuit board producing an analog pre-video signal;
   a pre-video conductor for transmitting said pre-video signal, said conductor having first and second ends, said first end connected to said first circuit board;
   a second circuit board lying in a second plane and longitudinally aligned with said first circuit board, said second circuit board being connected to said conductor at said second end thereof, said second circuit board including circuitry means for converting said pre-video signal to a post-video signal for reception by a standard video device; and a power supply electrically coupled with said first circuit board for driving said array of CMOS pixels, and said timing and control means, and electrically coupled to said second circuit board for driving said second circuit board.

2. A reduced area imaging device, as claimed in claim 1, further including:

a supplementary circuit board electrically coupled with said first and second circuit boards for enhancing said pre-video signal prior to reception by said second circuit board, said supplementary circuit board being longitudinally aligned with said first and second circuit boards and being positioned so as not to substantially extend beyond said profile area.

3. A reduced imaging device comprising:

an array of CMOS pixels defining a profile area and lying in a first plane, said array of CMOS pixels for receiving images thereon;

a circuit board longitudinally aligned with and electrically coupled to said array of CMOS pixels, said circuit board lying in a second plane which is offset from said first plane and substantially parallel to said first plane, said circuit board including circuitry means for timing and control of said array of CMOS pixels, said timing and control means producing an analog pre-video signal, said circuit board further including circuitry means for receiving said analog pre-video signal from said timing and control means and converting said pre-video signal to a post-video output signal for reception by a video device; and a power supply electrically coupled to said array of CMOS pixels, and said circuit board.

4. A device, as claimed in claim 3, further including:

a supplementary circuit board communicating with said array of CMOS pixels and said circuit board for enhancing said analog pre-video signal, said supplementary circuit board being longitudinally aligned with said array of CMOS pixels and said circuit board and being positioned so as not extend substantially beyond said profile area.

5. An endoscope with integral imaging capability comprising:

a tubular portion including a distal end, a proximal end and a central passageway extending therethrough;

a handle connected to said proximal end of said tubular portion for grasping by a surgeon;

at least one light fiber positioned around a periphery of said distal end for illuminating a surgical site;

a CMOS image sensor lying in a first plane and positioned at said distal end of said tubular portion for receiving images of the surgical site, said CMOS image sensor defining a profile area, and said CMOS image sensor producing an image signal;

circuitry means electrically coupled to said CMOS image sensor for timing and control of said CMOS image sensor, said circuitry means for timing and control placed within said tubular portion;

a video processor board spaced from and longitudinally aligned with said CMOS image sensor within said tubular portion and adjacent said distal end thereof, said video processor board lying in a second plane, said video processor board including circuitry means for processing said image signal and converting said image signal to a post-video signal, said video processor board being positioned so as not to extend substantially beyond said profile area;

a conductor connected between said CMOS image sensor and said video processor board for transmitting said image signal to said video processor board; and a power supply electrically coupled to said CMOS image sensor and said video processor board.

6. An endoscope, as claimed in claim 5, wherein:

said conductor includes a single conducting element.

7. An endoscope, as claimed in claim 5, wherein:

said timing and control means is placed adjacent said image sensor and on said first plane with said image sensor; and wherein said image signal is a pre-video signal.

8. An endoscope, as claimed in claim 5, wherein:

said timing and control means is placed on said second plane with said video processor board.

9. An endoscope, as claimed in claim 5, wherein:

said power supply is a battery attached to said handle.

10. A device, as claimed in claim 1, wherein:

said first plane is offset from and substantially parallel to said second plane.

11. A device, as claimed in claim 1, wherein:

said second circuit board is positioned so as not to extend substantially beyond said profile area of said first circuit board.

12. A device, as claimed in claim 1, wherein:

said means for converting said pre-video signal to a post-video signal is located on said second plane of said second circuit board.

13. An endoscope, as claimed in claim 5, further including:

a lens positioned at said distal end of said tubular portion and distally of said CMOS image sensor for producing a modified image on said CMOS image sensor.

14. An endoscope, as claimed in claim 5, wherein:

said CMOS image sensor lies in a first plane, and said video processor board lies in a second plane offset from and substantially parallel to said first plane.

15. An endoscope, as claimed in claim 5, wherein:

said video processor board is positioned in longitudinal alignment with said CMOS image sensor so that said video processor board does not extend substantially beyond said profile area.

* * * * *